(12) United States Patent
Johnson et al.

(10) Patent No.: US 7,763,769 B2
(45) Date of Patent: *Jul. 27, 2010

(54) BIOCOMPATIBLE WOUND DRESSING

(75) Inventors: Royce W. Johnson, Universal City, TX (US); David M. Tumey, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/409,116

(22) Filed: Apr. 21, 2006

(65) Prior Publication Data

US 2006/0189910 A1 Aug. 24, 2006

Related U.S. Application Data

(63) Continuation of application No. 10/075,743, filed on Feb. 14, 2002, now Pat. No. 7,070,584.

(60) Provisional application No. 60/269,657, filed on Feb. 16, 2001.

(51) Int. Cl.
*A61F 13/00* (2006.01)
*A61M 35/00* (2006.01)

(52) U.S. Cl. ............... 602/48; 602/41; 602/42; 602/46; 604/290; 604/313

(58) Field of Classification Search ............... 602/48; 424/443, 447, 448, 449
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |

(Continued)

FOREIGN PATENT DOCUMENTS

AU 550575 A1 8/1982

(Continued)

OTHER PUBLICATIONS

Chariker, Mark E., M.D., et al; "Effective Management of Incisional and cutaneous fistulae with closed suction wound drainage"; Contemporary Surgery, vol. 34, Jun. 1989, pp. 59-63.

(Continued)

*Primary Examiner*—Kim M Lewis

(57) ABSTRACT

A biocompatible wound dressing comprised of a pad for insertion substantially into a wound site and a wound drape for sealing enclosure of the foam pad at the wound site. The pad, comprised of a foam or other like material having relatively few open cells in contact with the areas upon which cell growth is to be encouraged so as to avoid unwanted adhesions, but having sufficiently numerous open cells so that drainage and negative pressure therapy may continue unimpaired, is placed in fluid communication with a vacuum source for promotion of fluid drainage, as known in the art. The pad is further comprised of an ultra-low density fused-fibrous ceramic, or a bioabsorbable branched polymer, or cell growth enhancing matrix or scaffolding.

39 Claims, 1 Drawing Sheet

U.S. PATENT DOCUMENTS

| | | |
|---|---|---|
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,118,470 A | 10/1978 | Casey et al. |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,595,713 A | 6/1986 | St. John |
| 4,605,399 A | 8/1986 | Weston et al. |
| 4,608,041 A | 8/1986 | Nielson |
| 4,614,794 A | 9/1986 | Easton et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,837,015 A | 6/1989 | Olsen |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,904,260 A | 2/1990 | Ray et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,077,049 A | 12/1991 | Dunn et al. |
| 5,085,861 A | 2/1992 | Gerhart et al. |
| 5,086,170 A | 2/1992 | Luheshi et al. |
| 5,092,858 A | 3/1992 | Benson et al. |
| 5,100,396 A | 3/1992 | Zamierowski |
| 5,102,983 A | 4/1992 | Kennedy |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,256,418 A | 10/1993 | Kemp et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,303,719 A | 4/1994 | Wilk et al. |
| 5,324,519 A | 6/1994 | Dunn et al. |
| 5,342,376 A | 8/1994 | Ruff |
| 5,344,415 A | 9/1994 | DeBusk et al. |
| 5,358,494 A | 10/1994 | Svedman |
| 5,368,859 A | 11/1994 | Dunn et al. |
| 5,437,622 A | 8/1995 | Carion |
| 5,437,651 A | 8/1995 | Todd et al. |
| 5,447,725 A | 9/1995 | Damani et al. |
| 5,449,383 A | 9/1995 | Chatelier et al. |
| 5,487,897 A | 1/1996 | Polson et al. |
| 5,527,293 A | 6/1996 | Zamierowski |
| 5,549,584 A | 8/1996 | Gross |
| 5,556,375 A | 9/1996 | Ewall |
| 5,578,662 A | 11/1996 | Bennett et al. |
| 5,599,552 A | 2/1997 | Dunn et al. |
| 5,607,388 A | 3/1997 | Ewall |
| 5,621,035 A | 4/1997 | Lyles et al. |
| 5,622,707 A | 4/1997 | Dorigatti et al. |
| 5,629,186 A | 5/1997 | Yasugawa et al. |
| 5,636,643 A | 6/1997 | Argenta et al. |
| 5,645,081 A | 7/1997 | Argenta et al. |
| 5,674,192 A | 10/1997 | Sahatijan et al. |
| 5,711,957 A | 1/1998 | Patat et al. |
| 5,711,958 A | 1/1998 | Cohn et al. |
| 5,717,030 A | 2/1998 | Dunn et al. |
| 5,759,570 A * | 6/1998 | Arnold .................... 424/443 |
| 5,780,281 A | 7/1998 | Yasukawa et al. |
| 5,795,584 A | 8/1998 | Totakura et al. |
| 5,824,335 A | 10/1998 | Dorigatti et al. |
| 5,834,188 A | 11/1998 | Harada et al. |
| 5,902,874 A | 5/1999 | Roby et al. |
| 5,902,875 A | 5/1999 | Roby et al. |
| 5,914,387 A | 6/1999 | Roby et al. |
| 5,932,716 A | 8/1999 | Sampath |
| 5,951,295 A | 9/1999 | Lyles et al. |
| 5,997,568 A | 12/1999 | Liu |
| 6,001,117 A | 12/1999 | Huxel et al. |
| 6,040,431 A | 3/2000 | Keck et al. |
| 6,071,267 A | 6/2000 | Zamierowski |
| 6,083,524 A | 7/2000 | Sawhney et al. |
| 6,087,479 A | 7/2000 | Stamler et al. |
| 6,090,544 A | 7/2000 | Harada et al. |
| 6,093,388 A | 7/2000 | Ferguson |
| 6,103,491 A | 8/2000 | Sampath |
| 6,110,460 A | 8/2000 | Sampath |
| 6,135,116 A | 10/2000 | Vogel et al. |
| 6,136,333 A | 10/2000 | Cohn et al. |
| 6,187,047 B1 | 2/2001 | Kwan et al. |
| 6,200,606 B1 | 3/2001 | Peterson et al. |
| 6,241,747 B1 | 6/2001 | Ruff |
| 6,255,277 B1 | 7/2001 | Stamler et al. |
| 6,287,316 B1 | 9/2001 | Agarwal et al. |
| 6,316,523 B1 | 11/2001 | Hyon et al. |
| 6,345,623 B1 | 2/2002 | Heaton et al. |
| 6,352,709 B1 | 3/2002 | Stamler et al. |
| 6,383,478 B1 | 5/2002 | Prokop et al. |
| 6,387,391 B1 | 5/2002 | Shikinami et al. |
| 6,392,974 B2 | 5/2002 | Shyu |
| 6,395,293 B2 | 5/2002 | Polson et al. |
| 6,407,060 B1 | 6/2002 | Charette et al. |
| 6,471,978 B1 | 10/2002 | Stamler et al. |

| | | | | | | |
|---|---|---|---|---|---|---|
| 6,479,643 | B1 | 11/2002 | Keck et al. | 2003/0113359 A1 | 6/2003 | Iyer et al. |
| 6,488,643 | B1 | 12/2002 | Tumey et al. | 2003/0118651 A1 | 6/2003 | Jampani et al. |
| 6,491,693 | B1 | 12/2002 | Lytinas | 2003/0125230 A1 | 7/2003 | Cohen et al. |
| 6,493,568 | B1 | 12/2002 | Bell et al. | 2003/0135148 A1 | 7/2003 | Dextradeur et al. |
| 6,498,142 | B1 | 12/2002 | Sampath et al. | 2003/0152522 A1 | 8/2003 | Miller et al. |
| 6,514,534 | B1 | 2/2003 | Sawhney | 2003/0152546 A1 | 8/2003 | Shalaby |
| 6,521,223 | B1 | 2/2003 | Calias et al. | 2003/0211793 A1 * | 11/2003 | Bell et al. .................. 442/123 |
| 6,553,998 | B2 | 4/2003 | Heaton et al. | 2003/0232087 A1 | 12/2003 | Lawin et al. |
| 6,565,871 | B2 | 5/2003 | Roser et al. | 2004/0001872 A1 | 1/2004 | Shih et al. |
| 6,566,345 | B2 | 5/2003 | Miller et al. | 2004/0006311 A1 | 1/2004 | Shchervinsky |
| 6,579,533 | B1 | 6/2003 | Törmälä et al. | 2004/0023842 A1 | 2/2004 | Pathak et al. |
| 6,599,518 | B2 | 7/2003 | Oster et al. | 2004/0037836 A1 | 2/2004 | Stamler et al. |
| 6,692,773 | B2 | 2/2004 | Burrell et al. | 2004/0039415 A1 | 2/2004 | Zamierowski |
| 6,696,499 | B1 | 2/2004 | Cohn et al. | 2004/0063606 A1 | 4/2004 | Chu et al. |
| 6,713,083 | B1 | 3/2004 | McGregor et al. | 2004/0063612 A1 | 4/2004 | Yalpani |
| 6,726,923 | B2 | 4/2004 | Iyer et al. | 2004/0093026 A1 | 5/2004 | Weidenhagen et al. |
| 6,780,890 | B2 | 8/2004 | Bassler et al. | 2004/0097402 A1 | 5/2004 | Bassler et al. |
| 6,814,079 | B2 | 11/2004 | Heaton et al. | 2004/0101564 A1 | 5/2004 | Rioux et al. |
| 6,893,424 | B2 | 5/2005 | Shchervinsky | 2004/0127475 A1 | 7/2004 | New et al. |
| 6,913,589 | B2 | 7/2005 | Dextradeur et al. | 2004/0127843 A1 | 7/2004 | Tu et al. |
| 6,939,568 | B2 | 9/2005 | Burrell et al. | 2004/0142888 A1 | 7/2004 | Manne et al. |
| 6,989,156 | B2 | 1/2006 | Gillis | 2004/0156819 A1 | 8/2004 | Cohn et al. |
| 7,008,647 | B2 | 3/2006 | Burrell et al. | 2004/0180829 A1 | 9/2004 | Bassler et al. |
| 7,025,990 | B2 | 4/2006 | Sawhney | 2004/0197409 A1 | 10/2004 | Iyer et al. |
| 7,041,868 | B2 * | 5/2006 | Greene et al. .................. 602/48 | 2004/0208845 A1 | 10/2004 | Michal et al. |
| 7,052,708 | B2 | 5/2006 | O'Leary | 2004/0213756 A1 | 10/2004 | Michal et al. |
| 7,070,584 | B2 * | 7/2006 | Johnson et al. ............. 604/313 | 2004/0217146 A1 | 11/2004 | Beck |
| 7,074,412 | B2 | 7/2006 | Weber | 2004/0253203 A1 | 12/2004 | Hossainy et al. |
| 7,166,570 | B2 | 1/2007 | Hunter et al. | 2004/0265475 A1 | 12/2004 | Hossainy et al. |
| 7,182,758 | B2 | 2/2007 | McCraw | 2005/0008609 A1 | 1/2005 | Cohn et al. |
| 7,201,925 | B2 | 4/2007 | Gillis | 2005/0019303 A1 | 1/2005 | Tsai et al. |
| 7,202,281 | B2 | 4/2007 | Cohn et al. | 2005/0027265 A1 | 2/2005 | Maki et al. |
| 7,216,651 | B2 | 5/2007 | Argenta et al. | 2005/0042197 A1 | 2/2005 | Shalaby |
| 7,241,736 | B2 | 7/2007 | Hunter et al. | 2005/0048121 A1 | 3/2005 | East et al. |
| 7,244,444 | B2 | 7/2007 | Bates | 2005/0063937 A1 | 3/2005 | Li et al. |
| 7,255,881 | B2 | 8/2007 | Gillis et al. | 2005/0106119 A1 | 5/2005 | Brandom et al. |
| 7,265,098 | B2 | 9/2007 | Miller et al. | 2005/0107756 A1 | 5/2005 | McCraw |
| 7,294,334 | B1 | 11/2007 | Michal et al. | 2005/0112087 A1 | 5/2005 | Musso et al. |
| 7,294,350 | B2 | 11/2007 | Marraccini | 2005/0112186 A1 | 5/2005 | Devore et al. |
| 7,306,903 | B1 | 12/2007 | Sampath et al. | 2005/0129624 A1 | 6/2005 | Burrell et al. |
| 7,326,426 | B2 | 2/2008 | Nathan et al. | 2005/0142163 A1 | 6/2005 | Hunter et al. |
| 7,342,048 | B2 | 3/2008 | Miyaji et al. | 2005/0147562 A1 | 7/2005 | Hunter et al. |
| 7,351,250 | B2 | 4/2008 | Zamierowski | 2005/0147599 A1 | 7/2005 | Hunter et al. |
| 7,361,168 | B2 | 4/2008 | Makower et al. | 2005/0147643 A1 | 7/2005 | Hunter et al. |
| 7,390,497 | B2 | 6/2008 | DesNoyer et al. | 2005/0148512 A1 | 7/2005 | Hunter et al. |
| 2001/0000728 | A1 | 5/2001 | Sawhney et al. | 2005/0158274 A1 | 7/2005 | Hunter et al. |
| 2001/0009662 | A1 | 7/2001 | Cohn et al. | 2005/0159364 A1 | 7/2005 | Cooper |
| 2001/0012511 | A1 | 8/2001 | Bezwada et al. | 2005/0159697 A1 | 7/2005 | Dextradeur et al. |
| 2001/0041743 | A1 | 11/2001 | Offenbacher et al. | 2005/0163822 A1 | 7/2005 | Shirahama et al. |
| 2001/0043943 | A1 | 11/2001 | Coffey | 2005/0169958 A1 | 8/2005 | Hunter et al. |
| 2001/0055622 | A1 | 12/2001 | Burrell et al. | 2005/0169959 A1 | 8/2005 | Hunter et al. |
| 2002/0001608 | A1 | 1/2002 | Polson et al. | 2005/0175657 A1 | 8/2005 | Hunter et al. |
| 2002/0010150 | A1 | 1/2002 | Cortese et al. | 2005/0175667 A1 | 8/2005 | Carlyle |
| 2002/0028181 | A1 | 3/2002 | Miller et al. | 2005/0177190 A1 | 8/2005 | Zamierowski |
| 2002/0055721 | A1 | 5/2002 | Palasis et al. | 2005/0182445 A1 | 8/2005 | Zamierowski |
| 2002/0072798 | A1 | 6/2002 | Riesle et al. | 2005/0186247 A1 | 8/2005 | Hunter et al. |
| 2002/0077661 | A1 | 6/2002 | Saadat | 2005/0187268 A1 | 8/2005 | Von Rechenberg et al. |
| 2002/0107223 | A1 | 8/2002 | Oster et al. | 2005/0191248 A1 | 9/2005 | Hunter et al. |
| 2002/0115951 | A1 | 8/2002 | Norstrem et al. | 2005/0208094 A1 | 9/2005 | Armitage et al. |
| 2002/0115952 | A1 | 8/2002 | Johnson et al. | 2005/0234510 A1 | 10/2005 | Zamierowski |
| 2002/0120185 | A1 | 8/2002 | Johnson | 2005/0238683 A1 | 10/2005 | Adhikari et al. |
| 2002/0143286 | A1 | 10/2002 | Tumey | 2005/0240147 A1 | 10/2005 | Makower et al. |
| 2002/0193336 | A1 | 12/2002 | Elkins et al. | 2005/0240220 A1 | 10/2005 | Zamierowski |
| 2003/0003127 | A1 | 1/2003 | Brown et al. | 2005/0244363 A1 | 11/2005 | Hossainy et al. |
| 2003/0027744 | A1 | 2/2003 | Dana et al. | 2005/0245906 A1 | 11/2005 | Makower et al. |
| 2003/0028140 | A1 | 2/2003 | Greff | 2005/0249697 A1 | 11/2005 | Uhrich et al. |
| 2003/0039697 | A1 | 2/2003 | Zhao et al. | 2005/0255079 A1 | 11/2005 | Santerre et al. |
| 2003/0060752 | A1 | 3/2003 | Bergheim et al. | 2005/0255082 A1 | 11/2005 | Santerre et al. |
| 2003/0072783 | A1 | 4/2003 | Stamler et al. | 2005/0266086 A1 | 12/2005 | Sawhney |
| 2003/0077242 | A1 | 4/2003 | Sawhney | 2005/0271617 A1 | 12/2005 | Shirahama et al. |
| 2003/0077311 | A1 | 4/2003 | Vyakarnam et al. | 2005/0277577 A1 | 12/2005 | Hunter et al. |
| 2003/0096734 | A1 | 5/2003 | Dehazya et al. | 2006/0024266 A1 | 2/2006 | Brandom et al. |
| 2003/0108511 | A1 | 6/2003 | Sawhney | 2006/0035861 A1 | 2/2006 | Berg et al. |

| | | | | | | |
|---|---|---|---|---|---|---|
| 2006/0051394 A1 | 3/2006 | Moore et al. | EP | 0117632 A2 | 9/1984 | |
| 2006/0052743 A1 | 3/2006 | Reynolds | EP | 0161865 A2 | 11/1985 | |
| 2006/0057179 A1 | 3/2006 | Giroux | EP | 0317780 A1 | 5/1989 | |
| 2006/0067908 A1 | 3/2006 | Ding | EP | 0358302 A2 | 3/1990 | |
| 2006/0115449 A1 | 6/2006 | Pacetti | EP | 0484387 | 2/1991 | |
| 2006/0120994 A1 | 6/2006 | Cotton et al. | EP | 0955969 | 1/1997 | |
| 2006/0135912 A1 | 6/2006 | Chernomorsky et al. | EP | 0842268 | 2/1997 | |
| 2006/0140904 A1 | 6/2006 | Wellisz et al. | EP | 0894004 | 9/1997 | |
| 2006/0142736 A1 | 6/2006 | Hissink et al. | EP | 0939639 | 1/1998 | |
| 2006/0147409 A1 | 7/2006 | Pathak et al. | EP | 1014998 | 1/1999 | |
| 2006/0147412 A1 | 7/2006 | Hossainy et al. | EP | 0943299 A1 | 9/1999 | |
| 2006/0148958 A1 | 7/2006 | Haraguchi et al. | EP | 1038538 A1 | 9/2000 | |
| 2006/0153796 A1 | 7/2006 | Fitz | EP | 1244725 | 6/2001 | |
| 2006/0177416 A1 | 8/2006 | Turnell et al. | EP | 1208850 A1 | 5/2002 | |
| 2006/0177417 A1 | 8/2006 | Musso et al. | EP | 1325753 A2 | 7/2003 | |
| 2006/0188545 A1 | 8/2006 | Hadba | EP | 1327460 A2 | 7/2003 | |
| 2006/0198815 A1 | 9/2006 | Barker et al. | EP | 1383522 | 1/2004 | |
| 2006/0216323 A1 | 9/2006 | Knaack et al. | EP | 1018967 B1 | 8/2004 | |
| 2006/0240063 A9 | 10/2006 | Hunter et al. | EP | 1457499 A1 | 9/2004 | |
| 2006/0240064 A9 | 10/2006 | Hunter et al. | EP | 1488748 A1 | 12/2004 | |
| 2006/0251612 A1 | 11/2006 | Kotzev et al. | EP | 1712252 A1 | 10/2006 | |
| 2006/0263330 A1 | 11/2006 | Emeta et al. | EP | 1738760 A1 | 1/2007 | |
| 2006/0280720 A1 | 12/2006 | Fitz et al. | EP | 1832302 A1 | 9/2007 | |
| 2006/0286063 A1 | 12/2006 | Shebuski et al. | EP | 1223981 B1 | 1/2008 | |
| 2006/0292077 A1 | 12/2006 | Zhao | FR | 2812551 A1 | 2/2002 | |
| 2007/0014752 A1 | 1/2007 | Roy et al. | FR | 2899479 A1 | 10/2007 | |
| 2007/0025955 A1 | 2/2007 | Lowinger et al. | GB | 692578 | 6/1953 | |
| 2007/0116666 A1 | 5/2007 | Cohn et al. | GB | 2 195 255 A | 4/1988 | |
| 2007/0128152 A1 | 6/2007 | Hadba et al. | GB | 2 197 789 A | 6/1988 | |
| 2007/0128153 A1 | 6/2007 | Hadba et al. | GB | 2 220 357 A | 1/1990 | |
| 2007/0128154 A1 | 6/2007 | Hadba et al. | GB | 2 235 877 A | 3/1991 | |
| 2007/0128155 A1 | 6/2007 | Seyedin et al. | GB | 2 333 965 A | 8/1999 | |
| 2007/0218124 A1 | 9/2007 | Devore et al. | GB | 2 329 127 B | 8/2000 | |
| 2007/0219497 A1 | 9/2007 | Johnson et al. | GB | 2415382 A | 12/2005 | |
| 2007/0225663 A1 | 9/2007 | Watt et al. | JP | 4129536 | 4/1992 | |
| 2007/0237750 A1 | 10/2007 | Naughton | SG | 71559 | 4/2002 | |
| 2007/0248643 A1 | 10/2007 | Devore et al. | WO | WO 80/02182 | 10/1980 | |
| 2007/0248676 A1 | 10/2007 | Stamler et al. | WO | WO 86/04235 A1 | 7/1986 | |
| 2007/0265585 A1 | 11/2007 | Joshi et al. | WO | WO 87/04626 | 8/1987 | |
| 2007/0265586 A1 | 11/2007 | Joshi et al. | WO | WO 90/10424 | 9/1990 | |
| 2007/0275033 A9 | 11/2007 | Moore et al. | WO | WO 91/01126 A1 | 2/1991 | |
| 2007/0280899 A1 | 12/2007 | Williams et al. | WO | WO 93/09727 | 5/1993 | |
| 2008/0003253 A1 | 1/2008 | Clauser | WO | WO 94/20041 | 9/1994 | |
| 2008/0003299 A1 | 1/2008 | Trotter et al. | WO | WO 94/22455 A1 | 10/1994 | |
| 2008/0004368 A1 | 1/2008 | Wang et al. | WO | WO 94/28935 A1 | 12/1994 | |
| 2008/0004578 A1 | 1/2008 | Hixon et al. | WO | WO 96/05873 | 2/1996 | |
| 2008/0014170 A1 | 1/2008 | Hnojewyj et al. | WO | WO 96/17606 A1 | 6/1996 | |
| 2008/0014286 A1 | 1/2008 | Gillis et al. | WO | WO 96/35416 A1 | 11/1996 | |
| 2008/0019969 A1 | 1/2008 | Gorman | WO | WO 96/38136 A1 | 12/1996 | |
| 2008/0031918 A1 | 2/2008 | Lawin et al. | WO | WO 96/40771 A1 | 12/1996 | |
| 2008/0031919 A1 | 2/2008 | Henson et al. | WO | WO 97/02794 A1 | 1/1997 | |
| 2008/0057024 A1 | 3/2008 | Zhang et al. | WO | WO 97/05241 A2 | 2/1997 | |
| 2008/0063620 A1 | 3/2008 | Cohn et al. | WO | WO 97/05285 A2 | 2/1997 | |
| 2008/0069865 A1 | 3/2008 | Southard et al. | WO | WO 97/18007 | 5/1997 | |
| 2008/0071234 A1 | 3/2008 | Kelch et al. | WO | WO 97/34626 A1 | 9/1997 | |
| 2008/0086110 A1 | 4/2008 | Galdonik et al. | WO | WO 97/36553 A1 | 10/1997 | |
| 2008/0095736 A1 | 4/2008 | Pathak et al. | WO | WO 97/37002 A1 | 10/1997 | |
| 2008/0097295 A1 | 4/2008 | Makower et al. | WO | WO 98/02171 A1 | 1/1998 | |
| 2008/0112921 A1 | 5/2008 | Chamness | WO | WO 99/02168 A1 | 1/1999 | |
| 2008/0154250 A1 | 6/2008 | Makower et al. | WO | WO 99/13793 | 3/1999 | |
| 2008/0160064 A1 | 7/2008 | Capelli et al. | WO | WO 00/09087 A1 | 2/2000 | |
| | | | WO | WO 00/45804 A2 | 8/2000 | |
| FOREIGN PATENT DOCUMENTS | | | WO | WO 00/56374 A1 | 9/2000 | |
| | | | WO | WO 01/12203 A1 | 2/2001 | |
| AU | 745271 | 4/1999 | WO | WO 01/30386 A1 | 5/2001 | |
| AU | 755496 | 2/2002 | WO | WO 01/51054 A2 | 7/2001 | |
| CA | 2005436 | 6/1990 | WO | WO 01/70199 A1 | 9/2001 | |
| DE | 26 40 413 A1 | 3/1978 | WO | WO 01/82863 A2 | 11/2001 | |
| DE | 43 06 478 A1 | 9/1994 | WO | WO 01/82937 A1 | 11/2001 | |
| DE | 295 04 378 U1 | 10/1995 | WO | WO 01/85664 A2 | 11/2001 | |
| DE | 69723429 T2 | 4/2004 | WO | WO 02/09729 A2 | 2/2002 | |
| DE | 60210441 T2 | 11/2006 | WO | WO 02/062335 A2 | 8/2002 | |
| EP | 0100148 A1 | 2/1984 | WO | WO 02/072020 A2 | 9/2002 | |

| | | |
|---|---|---|
| WO | WO 02/085384 A2 | 10/2002 |
| WO | WO 02/085385 A2 | 10/2002 |
| WO | WO 02/085386 A2 | 10/2002 |
| WO | WO 02/085387 A2 | 10/2002 |
| WO | WO 03/028590 A1 | 4/2003 |
| WO | WO 03/066705 A1 | 8/2003 |
| WO | WO 03/068245 A1 | 8/2003 |
| WO | WO 2004/002456 A1 | 1/2004 |
| WO | WO 2004/009147 A1 | 1/2004 |
| WO | WO 2004/009227 A2 | 1/2004 |
| WO | WO 2004/015130 A2 | 2/2004 |
| WO | WO 2004/019876 A2 | 3/2004 |
| WO | WO 2004/020011 A1 | 3/2004 |
| WO | WO 2004/028548 A2 | 4/2004 |
| WO | WO 2004/037311 A2 | 5/2004 |
| WO | WO 2004/041346 A1 | 5/2004 |
| WO | WO 2004/091592 A2 | 10/2004 |
| WO | WO 2004/110347 A2 | 12/2004 |
| WO | WO 2005/027957 A1 | 3/2005 |
| WO | WO 2005/039489 A2 | 5/2005 |
| WO | WO 2005/039537 A1 | 5/2005 |
| WO | WO 2005/041987 A1 | 5/2005 |
| WO | WO 2005/044285 A1 | 5/2005 |
| WO | WO 2005/046746 A2 | 5/2005 |
| WO | WO 2005/055950 A2 | 6/2005 |
| WO | WO 2005/058294 A1 | 6/2005 |
| WO | WO 2005/065079 A2 | 7/2005 |
| WO | WO 2005/077347 | 8/2005 |
| WO | WO 2005/082341 A2 | 9/2005 |
| WO | WO 2005/089778 A1 | 9/2005 |
| WO | WO 2005/110505 A2 | 11/2005 |
| WO | WO 2005/117755 A2 | 12/2005 |
| WO | WO 2005/123170 A1 | 12/2005 |
| WO | WO 2006/005939 A1 | 1/2006 |
| WO | WO 2006/019844 A1 | 2/2006 |
| WO | WO 2006/020180 A2 | 2/2006 |
| WO | WO 2006/028836 A1 | 3/2006 |
| WO | WO 2006/031922 A2 | 3/2006 |
| WO | WO 2006/055940 A2 | 5/2006 |
| WO | WO 2006/059237 A1 | 6/2006 |
| WO | WO 2006/063350 A2 | 6/2006 |
| WO | WO 2007/008927 A2 | 1/2007 |
| WO | WO 2007/014285 A2 | 2/2007 |
| WO | WO 2007/015964 A1 | 2/2007 |
| WO | WO 2007/019439 A2 | 2/2007 |
| WO | WO 2007/056316 A2 | 5/2007 |
| WO | WO 2007/060433 A1 | 5/2007 |
| WO | WO 2007/067621 A2 | 6/2007 |
| WO | WO 2007/067623 A2 | 6/2007 |
| WO | WO 2007/067625 A2 | 6/2007 |
| WO | WO 2007/067637 A2 | 6/2007 |
| WO | WO 2007/082331 A1 | 7/2007 |
| WO | WO 2007/084610 A2 | 7/2007 |
| WO | WO 2007/111925 A2 | 10/2007 |
| WO | WO 2007/124132 A2 | 11/2007 |
| WO | WO 2007/133618 A2 | 11/2007 |
| WO | WO 2007/133644 A2 | 11/2007 |
| WO | WO 2007/142683 A2 | 12/2007 |
| WO | WO 2008/006658 A1 | 1/2008 |
| WO | WO 2008/036361 A2 | 3/2008 |
| WO | WO 2008/048481 A2 | 4/2008 |
| WO | WO 2008/049029 A2 | 4/2008 |
| WO | WO 2008/063943 A2 | 5/2008 |
| WO | WO 2008/080128 A1 | 7/2008 |
| WO | WO 2008/086397 A2 | 7/2008 |

OTHER PUBLICATIONS

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastman, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., JR., "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

N.A. Bagautidinov, "Variant of External Vacuum Aspiration in the Treatment of Purulent Diseases of Soft Tissues," *Current Problems in Modern Clinical Surgery: Interdepartmental Collection*, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Dukić, ZŽ, Maksimović, D. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine and the Specialties: A Manual of Its Practical Application*, (W.B. Saunders Co., Philadelphia, PA 1909), pp. 17-25, 44-64, 90-96. 167-170, and 210-211.

Grandfils et al "Porous Biomaterials Tailored for Cell Culture," Cytotechnololgy 21(1): 7 (1006), Abstract.

International Search Report and Written Opinion for PCT/US08/00596 filed Jan. 17, 2005; Date Mailed: Jul. 16, 2008.

Non-Final Office Action dated Oct. 1, 2008 for U.S. Appl. No. 11/657,887.

Non-Final Office Action dated Dec. 3, 2003 for U.S. Appl. No. 10/161,076.

Response filed Jun. 2, 2004 to Non-Final Office Action dated Dec. 3, 2003 for U.S. Appl. No. 10/161,076.

RCE filed Sep. 28, 2004 for U.S. Appl. No. 10/161,076.

Final Office Action dated Dec. 15, 2004 for U.S. Appl. No. 10/161,076.

RCE and Response filed Jun. 15, 2005 to Final Office Action dated Dec. 15, 2004 for U.S. Appl. No. 10/161,076.

Non-Final Office Action dated Sep. 7, 2005 for U.S. Appl. No. 10/161,076.

Response filed Mar. 7, 2006 to Non-Final Office Action dated Sep. 7, 2005 for U.S. Appl. No. 10/161,076.

Final Office Action dated May 24, 2006 for U.S. Appl. No. 10/161,076.

RCE and Response filed Nov. 21, 2006 for U.S. Appl. No. 10/161,076.

Non-Final Office Action dated Feb. 12, 2007 for U.S. Appl. No. 10/161,076.

Non-Final Office Action dated Sep. 14, 2007 for U.S. Appl. No. 10/161,076.

Response filed Mar. 14, 2008 to Non-Final Office Action dated Sep. 14, 2007 for U.S. Appl. No. 10/161,076.

Final Office Action dated Jun. 20, 2008 for U.S. Appl. No. 10/161,076.

Response filed Dec. 22, 2008 to Non-Final Office Action dated Oct. 1, 2008 for U.S. Appl. No. 11/657,887.

Notice of Appeal filed Dec. 22, 2008 for U.S. Appl. No. 10/161,076.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Non-Final Action issued by the United States Patent and Trademark Office on Jun. 3, 2009 in U.S. Appl. No. 11/657,887.

Response filed Sep. 18, 2009 to United States Patent and Trademark Office Non-Final Action dated Jun. 3, 2009 in U.S. Appl. No. 11/657,887.

Notice of Allowance issued by the United States Patent and Trademark Office on Dec. 11, 2009 in U.S. Appl. No. 11/657,887.

Request for Continued Examination and Amendment filed on Jul. 22, 2009 in U.S. Appl. No. 10/161,076.

Non-Final Action issued by the United States Patent and Trademark Office on Aug. 25, 2009 in U.S. Appl. No. 10/161,076.

PCT International Search Report and Written Opinion issued on Jul. 16, 2009 in PCT International Application No. PCT/US 08/00596.

Response Filed Feb. 25, 2010 to Non-Final Action dated Aug. 25, 2009 in U.S. Appl. No. 10/161,076.

Re-Submission filed Mar. 15, 2010 of Feb. 25, 2010 Response to Office Action in U.S. Appl. No. 10/161,076.

Final Rejection date mailed Apr. 8, 2010 in U.S. Appl. No. 10/161,076.

\* cited by examiner

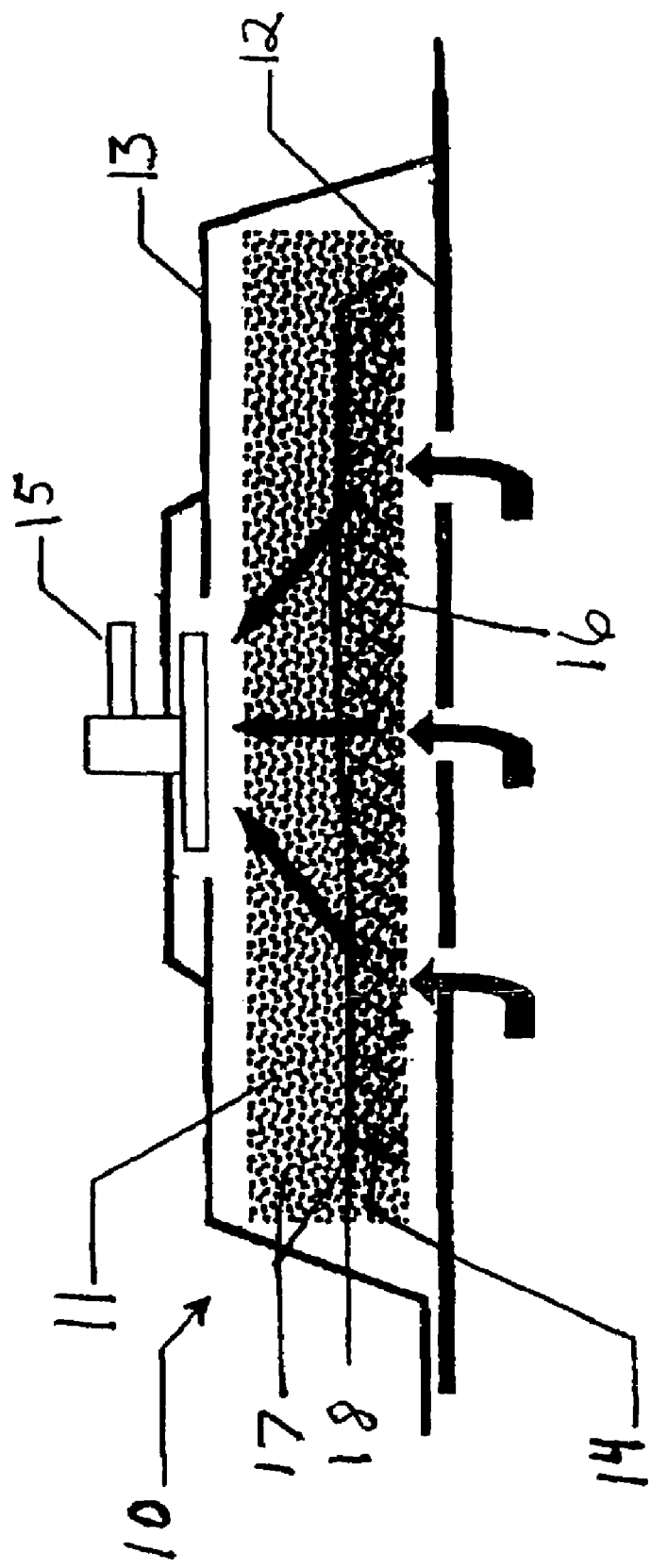

BIOCOMPATIBLE WOUND DRESSING

CROSS-REFERENCE TO RELATED APPLICATION

This is a continuing application of U.S. patent application Ser. No. 10/075,743 filed Feb. 14, 2002, now U.S. Pat. No. 7,070,584, which claims the benefit under 35 U.S.C. §119(e), of U.S. provisional patent application No. 60/269,657 filed Feb. 16, 2001.

FIELD OF THE INVENTION

This invention relates generally to wound dressings commonly associated with the vacuum induced healing of open wounds. More particularly, the present invention relates to a wound dressing, having a cell growth enhancing porous lattice, matrix, or scaffold, or a bioabsorbable layer as part of the dressing to enhance the wound healing.

BACKGROUND OF THE INVENTION

Vacuum induced healing of open wounds has recently been popularized by Kinetic Concepts, Inc. of San Antonio, Tex., by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31 1992, U.S. Pat. No. 5,261,893, issued Nov. 16, 1993, and U.S. Pat. No. 5,527,293, issued Jun. 18, 1996, the disclosures of which are incorporated herein by this reference. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are incorporated by reference as though fully set forth herein.

Substantial work has also been performed relating to the creation of bioabsorbable and includable, cell growth enhancing matrices, lattices, or scaffolds. Exemplary U.S. patents known to applicant include Kemp et al. U.S. Pat. No. 5,256,418 issued Oct. 26, 1993; Chatelier et al. U.S. Pat. No. 5,449,383 issued Sep. 12, 1995; Bennett et al. U.S. Pat. No. 5,578,662 issued Nov. 26, 1996; and two patents issued to Yasukawa et al. U.S. Pat. Nos. 5,629,186 issued May 13, 1997 and 5,780,281 issued Jul. 14, 1998, both from a common parent application; the disclosures of which are incorporated by reference herein.

As is well known to those of ordinary skill in the art, closure of surface wounds involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but also are also less able to successfully fight bacterial infection and thus are less able to naturally close the wound. Until the advent of vacuum induced therapy, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples may cause very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return.

While V.A.C.® therapy has been highly successful in the promotion of wound closure, healing many wounds previously thought largely untreatable, some difficulty remains. Because the very nature of V.A.C.® therapy dictates an atmospherically sealed wound site, the therapy must often be performed to the exclusion of other beneficial, and therefore desirable, wound treatment modalities. One of these hitherto excluded modalities is the encouragement of cell growth by the provision of an in situ cell growth-enhancing matrix.

Additional difficulty remains in the frequent changing of the wound dressing. As the wound closes, binding of cellular tissue to the wound dressing may occur. Use of traditional V.A.C.® therapy necessitates regular changing of the dressing. Reckless dressing changes can result in some tissue damage at the wound site if cellular tissue has grown excessively into the dressing.

Accordingly a primary object of the present invention is to provide an improved wound dressing for vacuum induced healing therapy, which overcomes the problems and limitations of the prior art.

A further object of the present invention is to provide a dressing that is also readily adaptable to a variety of wound sizes and shapes and that requires no inordinate modification of known procedures for administration of V.A.C.® therapy.

Another object is to provide a pad that enables the concurrent application of vacuum induced healing and cell growth enhancement in the treating of a wound by providing a bioabsorbable, or includable, porous cell growth enhancing matrix substrate thereupon.

An additional object of the present invention is to allow for controlled application of growth factors or other healing factors, which could be embedded in the dressing or introduced into the dressing through a port or other connector fitting.

Still another object of the present invention is to provide a fully and/or partially bioabsorbable wound dressing that minimizes disruption of the wound site during dressing changes.

A yet further object of the present invention is to provide such a dressing that is economical and disposable, but also safe for general patient use.

SUMMARY OF THE INVENTION

In accordance with the foregoing objects, the present invention generally comprises a foam pad for insertion substantially into the wound site and a wound drape for sealing enclosure of the foam pad at the wound site. The foam pad, comprised of a foam having relatively few open cells in contact with the areas upon which cell growth is to be encouraged so as to avoid unwanted adhesions, but having sufficiently numerous open cells so that drainage and V.A.C.® therapy may continue unimpaired, is placed in fluid communication with a vacuum source for promotion of fluid drainage, as known in the art. The foam pad is further comprised of a cell growth lattice, matrix, or scaffolding, all of which have been used in the art to describe similar constructs, is noninvasive to the known V.A.C.® therapy and requires no modification thereof. Additionally, or alternatively, the foam pad may be comprised of bioabsorbable polymers.

The foam pad of the present invention is provided with a bioabsorbable, or includable, fibrous growth-enhancing matrix. Numerous suitable materials for this purpose are known to the art, including collagen, dissolvable nylon, soluble plastics, and fibrous ceramic material. An exemplary fibrous ceramic material that may be utilized is an ultra-low density fused-fibrous ceramic manufactured by Materials Evolution and Development USA, Inc., under the trade name P.R.I.M.M.™ (Polymeric Rigid Inorganic Matrix Material), and further described in U.S. Pat. No. 5,951,295 issued on Sep. 14, 1999 to Lyles, et al., which is incorporated herein by reference. Additional materials may include alginates, fibrin gels, fused fibers and other similar materials utilized by those skilled in the art, that are capable of providing an invadable space and scaffolding for cellular growth. Alternatively, the growth-enhancing matrix may be non-fibrous, such as a gel-like growth-enhancing matrix. This matrix comprises a cell growth enhancing substrate that is up to over 90% open space. The fibers, or other particles, and spaces create nooks and crannies that provide an excellent environment to enhance cell growth, and thus further the process envisioned by the vacuum induced healing process.

Upon placement of the pad, having the cell growth enhancing substrate matrix embedded therein, an airtight seal is formed over the wound site to prevent vacuum leakage. In use the V.A.C.® therapy is conducted as known and, if desired, cell growth enhancement therapy is added by simply placing the matrix on the pad that is located within the wound. Given the addition of a suitable surface to which the fibrous lattice may be attached, the cell growth is channeled into the most desirable form and location, but is kept away from the pad itself. Utilization of bioabsorbable branched polymers in the pad itself, in addition to, or in place of the cell growth enhancing matrix, can allow the pad to remain in place during the healing process. As cell growth continues, the pad is absorbed, and there is no need to remove the pad.

An alternative embodiment comprises use of bioabsorbable branched polymers within a layer of the pad adjacent the wound, such that upon removal of the pad during dressing changes, the bioabsorbably branched polymer layer is left behind, leaving the wound site itself undisturbed. Additionally, the cell growth enhancing substrate matrix may be incorporated within the polymer layer to further enhance cellular growth at the wound site.

Accordingly, cell growth enhancement therapy may be conveniently combined with existing V.A.C.® therapies, without loss of V.A.C.® therapy performance and without inconvenience or overly increased cost.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which:

FIG. 1 shows, in partially cut away perspective view, the preferred embodiment of the present invention as applied to a mammalian wound site.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims that may be drawn hereto.

The present invention is a biocompatible wound dressing for use with negative pressure therapy. The term "wound" as used herein, may include burns, incisional wounds, excisional wounds, ulcers, traumatic wounds, and chronic open wounds. As used herein, the term "pad" refers to foam, screens, other porous-like materials. The term "conventional pad" refers to polyurethane (PU) or polyvinylalcohol (PVA) foams commonly used with V.A.C.® therapy. The term "V.A.C.® therapy" as used herein, refers to negative pressure wound therapy as commercialized by the assignee or its parent, and further described in the aforementioned patents and patent applications.

Referring now to the figures, the present invention 10 is shown to generally comprise a foam pad 11 for insertion substantially into the wound site 12 and a wound drape 13 for sealing enclosure of the foam pad 11 at the wound site 12. According to the invention, the foam pad 11 is modified to contain a cell growth-enhancing matrix, or lattice 14, whereby a desired highly porous cell growth enhancing substrate may be directed into and about the wound site 12. After insertion into the wound site 12 and sealing with the wound drape 13, the foam pad 11 is placed in fluid communication with a vacuum source for promotion of fluid drainage, as known to those of ordinary skill in the art. Foam pad 11 is modified from prior art pads in that the pad 11 comprises matrix 14 that is noninvasive to the known V.A.C.® therapy and therefore requires no modification thereof.

According to the preferred embodiment of the present invention, the foam pad 11, wound drape 13 and vacuum source are implemented as known in the prior art, with the exception of those modifications to the foam pad 11 detailed further herein. Each of these components is detailed in U.S. patent application Ser. No. 08/951,832 filed Oct. 16, 1997, which is a Continuation of U.S. patent application Ser. No. 08/517,901 filed Aug. 22, 1995, which is a Continuation-in-part of U.S. patent application Ser. No. 08/293,854 filed Aug. 22, 1994. By this reference, the full specification of U.S. patent application Ser. No. 08/951,832 ("the '832 application"), including the claims and the drawings, is incorporated as though fully set forth herein.

As detailed in the '832 application, the foam pad 11 preferably comprises a highly reticulated, open-cell polyurethane or polyether foam for good permeability of wound fluids while under suction. As also detailed in the '832 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '832 application also details the wound drape 13, which preferably comprises an elastomeric material at least peripherally covered with a pressure sensitive, acrylic adhesive for sealing application over the wound site 12.

According to the preferred method of the present invention, those components as are described in the '832 application are generally employed as known in the art with the exception that the foam pad 11 is provided with a matrix 14. This matrix 14 is shown to comprise porous material 16 that has been formed into a plurality of sections 17. The material 16 is implanted in the foam pad 11 at the base 18 of the pad 11. Because it is necessary to trim the foam pad 11 in preparation for V.A.C.® therapy wound treatment, material 16 preferably is placed in the central portion of pad 11. Applicant does not intend to limit itself to a regular or symmetrical arrangement of material 16 or sections 17 by use of the term "matrix".

Alternatively, or in addition to the preferred embodiment, the foam pad may be comprised of bioabsorbable branched polymers alone (not shown), or in combination with the matrix 14.

Upon placement of the pad 11, having the matrix 14 embedded therein, and/or protruding therefrom, and/or comprised of bioabsorbable branched polymers, the wound drape 13 is applied over the pad to form an airtight seal over the wound site. In use, the V.A.C.® therapy is conducted as known and, if desired, cell growth enhancement therapy is added by simply providing the matrix 14 comprising material 16. In this manner, cell growth enhancement therapy may be conveniently combined with existing V.A.C.® therapies, without loss of V.A.C.® therapy performance and without inconvenience or overly increased cost.

EXAMPLE I

The above described open celled foam is formed into a pad. The general principles set forth in U.S. Pat. No. 5,795,584 issued to Totakura et al on Aug. 18, 1998 at Col. 5 lines 5-42, are followed to create a structure superimposed on the bottom of the pad. Holes are placed in those portions of the non-bioabsorbable substrate relatively remote from the bioabsorbable cell growth enhancing matrix substrate. The matrix covers a portion of the pad located within the boundaries of the wound being treated. The pad is then completely covered by an airtight drape, and subjected to sub atmospheric pressure, as is the standard practice for utilizing V.A.C.® therapy. The matrix is absorbed within the expected useful life of the pad, so, that when the pad is removed, the matrix had been absorbed, and the growing cells are not disturbed. The pad is replaced, if necessary, either by a conventional pad or by a matrix containing pad, as deemed therapeutically necessary.

EXAMPLE II

A conventional pad is selected. A collagen cell growth matrix is applied to a portion of the bottom thereof. The general principles of V.A.C.® therapy are followed, with the matrix containing pad substituted for a conventional pad. During the expected duty cycle of the pad, the collagen matrix is absorbed by the growing cells, so that when the pad is removed, the matrix had been absorbed, and the growing cells are not disturbed. The pad is replaced, if necessary, either by a conventional pad or by a matrix containing pad, as deemed therapeutically necessary.

EXAMPLE III

The procedure set forth in EXAMPLE II is followed. However an ultra-low density fused-fibrous ceramic, sometimes referred to under the trademark P.R.I.M.M., is substituted for the collagen matrix thereof. The general principles of V.A.C.® therapy are followed. During the expected duty cycle of the pad, the ultra-low density fused-fibrous ceramic is absorbed by the growing cells, so, that when the pad is removed, the ultra-low density fused-fibrous ceramic had been absorbed, and the growing cells were not disturbed. The pad is replaced, if necessary, either by a conventional pad or by a matrix containing pad, as deemed therapeutically necessary.

EXAMPLE IV

Many suitable bioabsorbable materials have been used for sutures, surgical implements, and the like. A small sample of these materials are set forth in the following U.S. patents, to wit: U.S. Pat. No. 5,997,568, issued to Liu on Dec. 7, 1999 and the following patents issued in 1999 to Roby et al: U.S. Pat. Nos. 5,914,387; 5,902,874 and 5,902,875. A selected one or more of these, or similar materials, are placed upon a conventional pad. The general principles of V.A.C.® therapy are followed. During the expected duty cycle of the pad, the bioabsorbable material is absorbed by the growing cells, so, that when the pad is removed, the bioabsorbable material had been absorbed, and the growing cells were not disturbed. The pad is replaced, if necessary, either by a conventional pad or by a matrix containing pad, as deemed therapeutically necessary.

EXAMPLE V

A bioabsorbable branched polymer, similar to that described in U.S. Pat. No. 5,578,662 issued to Bennet et al., forms the pad. The general principles of V.A.C.® therapy are followed with the bioabsorbable branched polymer pad substituted for the conventional pad. During the expected duty cycle of the pad, the pad is absorbed by the growing cells, so that there is no need to replace the pad and disturb the wound site. If further treatment is deemed necessary, a conventional pad, or an additional matrix containing pad, or an additional bioabsorbable branched polymer pad may be placed in the wound site, and V.A.C.® therapy continued.

While the foregoing description is exemplary of the preferred embodiment of the present invention, those of ordinary skill in the relevant arts will recognize the many variations, alterations, modifications, substitutions and the like are readily possible, especially in light of this description and the accompanying drawings. In any case, because the scope of the present invention is much broader than any particular embodiment, the foregoing detailed description should not be construed as a limitation of the scope of the present invention, which is limited only by the claims that are drawn hereto.

We claim:

1. A biocompatible wound dressing, comprising:
   a biocompatible pad shaped to conform to a wound site;
   an air-tight seal removably adhered to said pad;
   a negative pressure source in fluid communication with said pad;
   a scaffold removably connected to a wound-contacting surface of the pad, the scaffold being adapted to facilitate cellular growth from the wound into the scaffold.

2. The biocompatible wound dressing of claim 1 wherein the biocompatible pad comprises an open-cell reticulated porous foam.

3. The biocompatible wound dressing of claim 1, further comprising a flexible tube communicating between said pad and said negative pressure source.

4. The biocompatible wound dressing of claim 3 further comprising a removable canister in fluid communication between said pad and said negative pressure source.

5. A biocompatible wound dressing comprising:
   a pad comprised of a non-bioabsorbable substrate and a scaffold, the pad being shaped to conform to a wound site, the scaffold adapted to be absorbed or included by the wound, the scaffold being removably connected to a wound-contacting surface of the non-bioabsorbable substrate and adapted to allow cellular growth through the scaffold;
   an air-tight-seal removably adhered to said pad; and
   a negative pressure source in fluid communication with said scaffold.

6. The biocompatible wound dressing of claim 5 further comprising a flexible tube communicating between said pad and said negative pressure source.

7. The biocompatible wound dressing of claim 6 further comprising a removable canister in fluid communication between said pad and said negative pressure source.

8. A biocompatible wound dressing comprising:
   a first pad comprised of a bioabsorbable or includable cell-growth enhancing matrix, shaped to conform to a wound site;
   the bioabsorbable or includable cell-growth enhancing matrix comprising porous, highly reticulated material, the matrix being adapted to contact the wound surface and to be absorbed or included by the wound;
   a negative pressure source in fluid communication with said pad;
   a second pad comprised of a bioabsorbable or includable cell-growth enhancing matrix, adapted to connect to the surface of the first pad opposite the wound-facing surface and to cover the first pad when the first pad is partially absorbed or included by the wound; and
   the bioabsorbable or includable cell-growth enhancing matrix of the second pad comprising porous, highly reticulated material, the matrix being adapted to contact the wound surface and to be absorbed or included by the wound;
   wherein the matrix of the second pad is adapted to facilitate cellular growth from the wound through the matrix;
   wherein the matrix of the first pad is adapted to facilitate cellular growth from the wound through the matrix.

9. The biocompatible wound dressing of claim 8 further comprising a removable canister in fluid communication between said pad and said negative pressure source.

10. The biocompatible wound dressing of claim 8, further comprising a third pad comprised of a non-bioabsorbable substrate removable coupled to the second pad, wherein the substrate defines a plurality of holes remote from the cell-growth enhancing matrices.

11. A biocompatible wound dressing comprising:
    a pad comprised of a non-bioabsorbable substrate, and a bioabsorbable or includable cell-growth enhancing matrix removably coupled to the non-bioabsorbable substrate, the pad being shaped to conform to a wound site;
    the cell-growth enhancing matrix comprising reticulated porous material formed into a plurality of sections and implanted into the substrate in the central portion of the pad, the matrix being adapted to contact the wound surface and to be absorbed or included by the wound;
    the substrate defining a plurality of holes remote from the bioabsorbable or includable cell-growth enhancing matrix; and
    wherein the pad is adapted to be fluidly connected to a negative pressure source.

12. The biocompatible wound dressing of claim 11 further comprising a removable canister in fluid communication between said pad and said negative pressure source.

13. The biocompatible wound dressing according to claim 11 further comprising a seal removably adhered to the pad.

14. The biocompatible wound dressing according to claim 11, wherein the matrix component provides an invadable space and scaffolding for cellular growth.

15. The biocompatible wound dressing according to claim 12, wherein the matrix is chosen from the group of collagen, dissolvable nylon, soluble plastics, fibrous ceramics, alginates, fibrin gels, fused fibers, and branched polymers.

16. The biocompatible wound dressing according to claim 12, wherein the non-bioabsorbable substrate is a polyurethane foam.

17. The biocompatible wound dressing according to claim 12, wherein the non-bioabsorbable substrate is a polyvinylalcohol foam.

18. A biocompatible wound dressing comprising:
    a bioabsorbable or includable matrix having a surface adapted to be placed in contact with a tissue site at which new cell growth is desired, the bioabsorbable or includable matrix having an invadable space to facilitate cellular growth from the tissue site into the bioabsorbable or includable matrix;
    a non-bioabsorbable porous substrate removably connected to the matrix; and
    a flexible tube in fluid communication with at least one of the matrix and the substrate, the flexible tube further being adapted to be fluidly connected to a negative pressure source.

19. The biocompatible wound dressing according to claim 18 further comprising a seal removably adhered to the substrate.

20. The biocompatible wound dressing according to claim 18, wherein the matrix component provides an invadable space and scaffolding for cellular growth.

21. The biocompatible wound dressing according to claim 18, wherein the matrix is chosen from the group of collagen, dissolvable nylon, soluble plastics, fibrous ceramics, alginates, fibrin gels, fused fibers, and branched polymers.

22. The biocompatible wound dressing according to claim 18, wherein the substrate is a polyurethane foam.

23. The biocompatible wound dressing according to claim 18, wherein the substrate is a polyvinylalcohol foam.

24. A biocompatible wound dressing comprising:
a bioabsorbable pad having a surface adapted to be placed in contact with a tissue site at which new cell growth is desired, the bioabsorbable pad having an invadable space to facilitate cellular growth from the tissue site into the bioabsorbable pad; and
a flexible tube in fluid communication with the bioabsorbable pad, the flexible tube further being adapted to be fluidly connected to a negative pressure source, the flexible tube delivering negative pressure to the bioabsorbable pad.

25. The biocompatible wound dressing according to claim 24, wherein the bioabsorbable pad is a bioabsorbable branched polymer.

26. The biocompatible wound dressing according to claim 24 further comprising a seal removably adhered to the pad.

27. The biocompatible wound dressing according to claim 24, wherein the bioabsorbable pad is porous to allow distribution of negative pressure to the tissue site.

28. The biocompatible wound dressing according to claim 24 further comprising a removable canister in fluid communication with the flexible tube.

29. A method of providing negative pressure therapy to a wound comprising:
positioning a pad having a bioabsorbable or includable component and a non-bioabsorbable component adjacent a wound such that the bioabsorbable or includable component contacts the wound;
delivering a negative pressure to the wound through the pad to promote growth of new cells at the wound and within the bioabsorbable or includable component; and
removing the non-bioabsorbable component following delivery of the negative pressure.

30. The method according to claim 29 further comprising:
allowing the bioabsorbable or includable component to remain in the wound following removal of the non-bioabsorbable component.

31. The method according to claim 29 further comprising:
positioning a second pad having a non-bioabsorbable component in contact with the bioabsorbable or includable component of the first pad.

32. The method according to claim 29 further comprising:
positioning a second pad having a bioabsorbable or includable component and a non-bioabsorbable component within the wound such that the bioabsorbable or includable component of the second pad contacts the bioabsorbable or includable component of the first pad;
delivering a negative pressure to the second pad to promote growth of new cells within at least one of the bioabsorbable or includable component of the first pad and the bioabsorbable or includable component of second pad.

33. The method according to claim 32 further comprising:
removing the non-bioabsorbable component of the second pad following delivery of the negative pressure.

34. The method according to claim 29 further comprising:
covering the wound and pad with a drape to assist in maintaining the negative pressure at the wound.

35. The method according to claim 29, wherein the negative pressure is sub atmospheric pressure.

36. The method according to claim 29, wherein the bioabsorbable or includable component is capable of providing an invadable space and scaffolding for cellular growth.

37. The method according to claim 29, wherein the bioabsorbable or includable component is chosen from the group of collagen, dissolvable nylon, soluble plastics, fibrous ceramics, alginates, fibrin gels, fused fibers, and branched polymers.

38. The method according to claim 29, wherein the non-bioabsorbable component is a polyurethane foam.

39. The method according to claim 29, wherein the non-bioabsorbable component is a polyvinylalcohol foam.

* * * * *